United States Patent
Feger

(10) Patent No.: US 6,562,255 B1
(45) Date of Patent: May 13, 2003

(54) CONDUCTIVE ELECTROLYTE FOR HIGH VOLTAGE CAPACITORS

(75) Inventor: Christopher Feger, Easley, SC (US)

(73) Assignee: Pacesetter, Inc., Sunnyvale, CA (US)

( * ) Notice: Subject to any disclaimer, the term of this patent is extended or adjusted under 35 U.S.C. 154(b) by 165 days.

(21) Appl. No.: 09/812,331

(22) Filed: Mar. 19, 2001

(51) Int. Cl.$^7$ .............................................. H01G 9/035
(52) U.S. Cl. ...................... 252/62.2; 361/506; 361/504; 607/5; 429/326; 429/339; 429/341; 429/343
(58) Field of Search .................... 252/62.2; 361/506, 361/504; 607/5; 429/326, 339, 341, 343

(56) References Cited

U.S. PATENT DOCUMENTS

| | | | |
|---|---|---|---|
| 4,860,169 A | 8/1989 | Dapo | ......................... 361/506 |
| 5,131,388 A | 7/1992 | Pless et al. | ............. 128/419 D |
| 5,687,057 A | * 11/1997 | Dapo | ......................... 361/506 |

* cited by examiner

Primary Examiner—C. Melissa Koslow
(74) Attorney, Agent, or Firm—Steven M. Mitchell

(57) ABSTRACT

The present invention is directed to a conductive electrolyte for use in high voltage electrolytic capacitors and to an electrolytic capacitor impregnated with the electrolyte of the present invention for use in an implantable cardioverter defibrillator (ICD). The electrolyte according to the present invention is composed of a two solvent mixture of ethylene glycol and di(ethylene glycol); a combination of boric acid with an aliphatic dicarboxylic acid of carbon chain length from eight to thirteen, such as suberic, azelaic, sebacic, undecanedioic, dodecanedioic, or brassylic acid; a very long chain dicarboxylic acid, where the acid moieties are separated by 34 carbons; and a nitro-substituted aromatic compound as a degassing agent, such as 3-nitroacetophenone or 2-nitroanisole. This electrolyte is then titrated with a light amine such as ammonia, diethylamine, dimethylamine, trimethylamine, or triethylamine. The electrolyte according to the present invention, when impregnated in an electrolytic capacitor, provides an acceptable breakdown voltage while having a reasonable bulk conductivity. This electrolyte, when impregnated within a capacitor constructed of appropriate foils and paper spacers, should provide a part with a working voltage of at least 500 volts, while having a bulk conductivity of approximately 3 mS/cm.

22 Claims, No Drawings

CONDUCTIVE ELECTROLYTE FOR HIGH VOLTAGE CAPACITORS

BACKGROUND OF THE INVENTION

1. Field of the Invention

The present invention is directed to a conductive electrolyte for high voltage electrolytic capacitors and to an electrolytic capacitor impregnated with the electrolyte of the present invention for use in an implantable cardioverter defibrillator (ICD).

2. Related Art

Compact, high voltage capacitors are utilized as energy storage reservoirs in many applications, including implantable medical devices. These capacitors are required to have a high energy density since it is desirable to minimize the overall size of the implanted device. This is particularly true of an Implantable Cardioverter Defibrillator (ICD), also referred to as an implantable defibrillator, since the high voltage capacitors used to deliver the defibrillation pulse can occupy as much as one third of the ICD volume.

Implantable Cardioverter Defibrillators, such as those disclosed in U.S. Pat. No. 5,131,388, incorporated herein by reference, typically use two electrolytic capacitors in series to achieve the desired high voltage for shock delivery. For example, an implantable cardioverter defibrillator may utilize two 350 to 400 volt electrolytic capacitors in series to achieve a voltage of 700 to 800 volts.

Electrolytic capacitors are used in ICDs because they have the most nearly ideal properties in terms of size, reliability and ability to withstand relatively high voltage. Conventionally, such electrolytic capacitors include an etched aluminum foil anode, an aluminum foil or film cathode, and an interposed kraft paper or fabric gauze separator impregnated with a solvent-based liquid electrolyte. While aluminum is the preferred metal for the anode plates, other metals such as tantalum, magnesium, titanium, niobium, zirconium and zinc may be used. A typical solvent-based liquid electrolyte may be a mixture of a weak acid and a salt of a weak acid, preferably a salt of the weak acid employed, in a polyhydroxy alcohol solvent. The electrolytic or ion-producing component of the electrolyte is the salt that is dissolved in the solvent. The entire laminate is rolled up into the form of a substantially cylindrical body, or wound roll, that is held together with adhesive tape and is encased, with the aid of suitable insulation, in an aluminum tube or canister. Connections to the anode and the cathode are made via tabs. Alternative flat constructions for aluminum electrolytic capacitors are also known, comprising a planar, layered, stack structure of electrode materials with separators interposed therebetween, such as those disclosed in the above-mentioned U.S. Pat. No. 5,131,388.

There are numerous commercially available compositions of electrolyte for use in electrolytic capacitors that can confirm to reasonable specifications, as long as the operating voltage of the capacitor remains at 400 volts or lower. However, once this limit is exceeded, the choices become somewhat more limited. Many high voltage electrolytes employ the use of very long chain dicarboxylic acids and large bases to achieve the necessary breakdown voltages, however, the resultant electrolytes have very low conductivities ($\leq 1$ mS/cm). For example, U.S. Pat. No. 4,860,169 to Dapo discloses an electrolytic capacitor for use in operation at voltages above 500 volts, produced by employing an electrolyte containing a straight chain saturated aliphatic dicarboxylic acid in which the carboxylic moieties are separated by at least 14 carbon atoms. In particular, an electrolyte for use in electrolytic capacitors is disclosed consisting essentially of a solution of a straight chain saturated aliphatic dicarboxylic acid in which the carboxylics are separated by at least 14 carbon atoms in a mixture of at least one polar organic solvent and at least water in an amount of from 4–30% by weight of the organic solvent or a borate in an amount of 2–5% by weight of the organic solvent.

Therefore, what is needed in the art is an electrolyte that provides acceptable breakdown characteristics with reasonable conductivity when impregnated in an electrolytic capacitor operating above 400 volts.

SUMMARY OF THE INVENTION

The present invention is directed to a conductive electrolyte for use in high voltage electrolytic capacitors and to an electrolytic capacitor impregnated with the electrolyte of the present invention for use in an implantable cardioverter defibrillator (ICD). The electrolyte according to the present invention is composed of a two solvent mixture of ethylene glycol and di(ethylene glycol); a combination of boric acid with an aliphatic dicarboxylic acid of carbon chain length from eight to thirteen, such as suberic, azelaic, sebacic, undecanedioic, dodecanedioic, or brassylic acid; a very long chain dicarboxylic acid, where the acid moieties are separated by 34 carbons (referred to as "dimer acid"); and a nitro-substituted aromatic compound as a degassing agent, such as 3-nitroacetophenone or 2-nitroanisole. This electrolyte is then titrated with a light amine such as ammonia, diethylamine, dimethylamine, trimethylamine, or triethylamine. A representative composition according to the present invention that displays the desired properties is: 64.1% by weight ethylene glycol, 27.5% by weight di(ethylene glycol), 1.8% by weight dimer acid, 3.4% by weight azelaic acid, 0.9% by weight boric acid, 0.9% by weight 3-Nitroacetophenone, and 1.4% by weight ammonium hydroxide (28–30% w/w).

The electrolyte according to the present invention, when impregnated in an electrolytic capacitor, provides an acceptable breakdown voltage while having a reasonable bulk conductivity. This is accomplished by combining the superior conductivity characteristics of an eight to thirteen carbon chain dicarboxylic acid, with the high breakdown strength characteristics of a very long chain dicarboxylic acid, where the acid moieties are separated by 34 carbons. This electrolyte, when impregnated within a capacitor constructed of appropriate foils and paper spacers, should provide a part with a working voltage of at least 500 volts, while having a bulk conductivity of approximately 3 mS/cm.

DETAILED DESCRIPTION OF THE PREFERRED EMBODIMENTS

The present invention is directed to a conductive electrolyte for use in high voltage electrolytic capacitors and to an electrolytic capacitor impregnated with the electrolyte of the present invention for use in an ICD. In particular, the electrolyte according to the present invention, when impregnated in an electrolytic capacitor, provides an acceptable breakdown voltage while having a reasonable bulk conductivity. The electrolyte according to the present invention may be used in a capacitor operating above 400 VDC.

Preferred embodiments of the present invention are now described. While specific configurations and arrangements are discussed, it should be understood that this is done for illustrative purposes only. A person skilled in the relevant art will recognize that other configurations and arrangements can be used without departing from the spirit and scope of the invention. It will be apparent to a person skilled in the relevant art that this invention can also be employed in a variety of other devices and applications.

The electrolyte according to the present invention is composed of a two solvent mixture of ethylene glycol and di(ethylene glycol); a combination of boric acid with an aliphatic dicarboxylic acid of carbon chain length from eight to thirteen, such as suberic, azelaic, sebacic, undecanedioic, dodecanedioic, or brassylic acid; a very long chain dicarboxylic acid, where the acid moieties are separated by 34 carbons, such as dimer acid; and a nitro-substituted aromatic compound as a degassing agent, such as 3-nitroacetophenone or 2-nitroanisole. This electrolyte is then titrated with a light amine such as ammonia, diethylamine, dimethylamine, trimethylamine, or triethylamine. A representative composition according to the present invention that displays the desired properties is: 64.1% by weight ethylene glycol, 27.5% by weight di(ethylene glycol), 1.8% by weight dimer acid, 3.4% by weight azelaic acid, 0.9% by weight boric acid, 0.9% by weight 3-Nitroacetophenone, and 1.4% by weight ammonium hydroxide (28–30% w/w). This composition provides an open cup scintillation voltage of 465 volts, a conductivity of 3.0 mS/cm at 37° C. (resistivity of 330 Ω-cm), a pH of 9.5, and water content of 1.65% by Karl Fischer titration. This composition can have working tolerances of 60–75% by weight ethylene glycol, 10–35% by weight di(ethylene glycol), 0.5–3.0% by weight dimer acid, 2.0–5.0% by weight $C_8$ to $C_{13}$ dicarboxylic acid, 0.0–2.0% by weight boric acid, 0.5–1.5% by weight degassing agent and 1–4% by weight ammonium hydroxide (28–30% w/w).

An electrolytic capacitor according to the present invention is constructed of anode and cathode layers, stacked with a paper insulator or spacer between each layer. The anode layer is composed of one or more anode foils stacked together without any paper spacer, to form a high energy density anode element. The anode and cathode layers are then grouped together in a parallel connection to produce sufficient capacitance for the intended function. This finished stack is inserted into a case with a geometry closely following the contour of the stack, and designed to minimize the space occupied inside the finished defibrillator.

Aluminum foil is preferred for the anode and cathode layers, because of its ability to produce a sufficient quality oxide layer, its conductive properties, and its wide commercial availability. Other valve metal foils conventionally utilized in electrolytic capacitors could also be used, including titanium, tantalum, magnesium, niobium, zirconium and zinc. Preferably, a strip of unetched, high purity (99.99%) aluminum foil with a cubicity of greater than 85% in the <100> direction is used. Such foils are well-known in the art and are readily available from commercial sources known to those skilled in the art.

The anode foil is etched in an aqueous halide based etch solution, typically a hydrochloric acid or sodium chloride solution, according to a conventional etch process; for example, U.S. Pat. No. 5,715,133 to Harrington et al. describes a suitable method of etching foil and is incorporated herein by reference in its entirety. The etch solution preferably consists of about 1.3% by weight sodium chloride, 3.5% by weight sodium perchlorate, 0.35% sodium persulfate, and deionized water. The etch solution preferably is heated to 60° C. to 95° C., more preferably 85° C. The foil is etched at a DC current density of about 0.01 A/cm$^2$ to 0.30 A/cm$^2$, preferably 0.15 A/cm$^2$. A charge of 20 to 100 coulombs per cm2 is passed through the foil during the etching process, with about 50 coulombs/cm$^2$ preferred, which requires a time of about 2 minutes and 13 seconds to 11 minutes and 7 seconds, with about 5 minutes and 30 seconds preferred.

The foil is then removed from the etch solution and rinsed in deionized water. Then the tunnels formed during the initial etch are widened, or enlarged, in a secondary etch solution, typically an aqueous based nitrate solution, preferably between 1 to 20% aluminum nitrate, more preferably between 10 to 14% aluminum nitrate, with less than 1% free nitric acid. The etch tunnels are widened to an appropriate diameter by methods known to those in the art, such as that disclosed in U.S. Pat. No. 4,518,471 to Arora and U.S. Pat. No. 4,525,249 to Arora, entirely incorporated herein by reference.

After the etch tunnels have been widened, the foil is again rinsed with deionized water and dried. Finally, a barrier oxide layer may be formed onto one or both surfaces of the metal foil by placing the foil into an electrolyte bath and applying a positive voltage to the metal foil and a negative voltage to the electrolyte. The barrier oxide layer provides a high resistance to current passing between the electrolyte and the metal foils in the finished capacitor, also referred to as the leakage current. A high leakage current can result in the poor performance and reliability of an electrolytic capacitor. In particular, a high leakage current results in greater amount of charge leaking out of the capacitor once it has been charged.

The formation process consists of applying a voltage to the foil through an electrolyte such as boric acid and water or other solutions familiar to those skilled in the art, resulting in the formation of an oxide on the surface of the anode foil. The preferred electrolyte for formation is a 100–1000 $\mu$S/cm, preferably 500 $\mu$S/cm, citric acid concentration. In the case of an aluminum anode foil, the formation process results in the formation of aluminum oxide ($Al_2O_3$) on the surface of the anode foil. The thickness of the oxide deposited or "formed" on the anode foil is proportional to the applied voltage, roughly 10 to 15 Angstroms per applied volt.

The etched and formed anode foils are cut and the capacitor assembled as discussed above. An electrolytic capacitor stack according to the present invention consists of a number of units of: cathode, a paper spacer, one or more anodes, a paper spacer and cathode; with neighboring units sharing the cathode between them.

The electrolyte of the present invention is then prepared. Initially, the ethylene glycol, di(ethylene glycol) and very long chain dicarboxylic acid, where the acid moieties are separated by 34 carbons, such as dimer acid, are mixed and heated. During heating, at 60–100° C., preferably 90° C., boric acid and an aliphatic dicarboxylic acid of carbon chain length from eight to thirteen, such as suberic, azelaic, sebacic, undecanedioic, dodecanedioic, or brassylic acid, are added to the solution and dissolved. The solution is then heated to 120° C. and held at 120° C.–130° C. for one hour. After heating, a nitro-substituted aromatic compound, such as 3-nitroacetophenone or 2-nitroanisole, is added to the solution as a degassing agent and the solution is allowed to cool to room temperature. The solution is then titrated with a light amine including ammonia, diethylamine, triethylamine, or triethanolamine, to a pH range of 8–11, preferably 9.5. A representative composition according to the present invention consists of 64.1% by weight ethylene glycol, 27.5% by weight di(ethylene glycol), 1.8% by weight dimer acid, 3.4% by weight azelaic acid, 0.9% by weight boric acid, 0.9% by weight 3-Nitroacetophenone, and 1.4% by weight ammonium hydroxide (28–30% w/w).

The pre-assembled capacitor is then vacuum impregnated with the electrolyte of the present invention, by placing the capacitor in contact with the electrolyte and reducing the pressure to less than 50 cm Hg. The capacitor is held at this low pressure for 5 to 45 minutes with a preferred time of 15 minutes, and then pressure is restored, using the pressure to force the electrolyte mixture into the capacitor stack. The capacitor is then removed and placed in a 65 to 90° C. oven with a preferred temperature of 90° C. and a maximum oxygen atmospheric concentration of 2% for a period of 2 to 24 hours, with a preferred time of 4 hours. The capacitor is then aged in a normal manner by applying the working voltage to the capacitor, allowing the capacitor to reach this voltage, and then allowing the current to decrease.

Electrolytic capacitors according to the present invention can be incorporated into implantable medical devices, such as implantable cardioverter defibrillators (ICDs), as would be apparent to one skilled in the art, as described in U.S. Pat. No. 5,522,851 issued to Fayram.

Having now generally described the invention, the same will be more readily understood through reference to the following example which are provided by way of illustration, and are not intended to be limiting of the present invention.

EXAMPLE

An electrolyte was prepared having the following formulation:

| | |
|---|---|
| Ethylene Glycol | 108.7g |
| Di(ethylene Glycol) | 46.5g |
| Dimer Acid | 3.3g |
| Azelaic Acid | 5.7g |
| Boric Acid | 1.5g |
| Nitroacetophenone | 1.5g |
| Ammonia | 2.4g |

The ethylene glycol and di(ethylene glycol) solvents and dimer acid were mixed and heated in a 200 mL beaker. At 90° C., the azelaic acid and boric acid were added and dissolved. The solution was heated to 120° C. and held for one hour at 120° C.–130° C. The hot plate was switched off and the nitroacetophenone was stirred in. The beaker was removed from the hot plate and allowed to cool to room temperature, when the aqueous ammonia was added. The dimer acid remained as an oil and the anhydrous ammonia was bubbled in to aid dissolution. A pH (at 36.5° C.) of 9.51 was observed and a conductivity of 3.00 mS/cm was obtained. An open cup scintillation voltage (at 38.4° C.) of approximately 465V was obtained and water content of 1.65% was observed by Karl Fischer titration.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents. Additionally, all references cited herein, including journal articles or abstracts, published or corresponding U.S. or foreign patent applications, issued U.S. or foreign patents, or any other references, are each entirely incorporated by reference herein, including all data, tables, figures, and text presented in the cited references.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A conductive electrolyte for high voltage electrolytic capacitors, comprising:
   ethylene glycol;
   di(ethylene glycol);
   boric acid;
   an aliphatic dicarboxylic acid of carbon chain length from eight to thirteen;
   a very long chain dicarboxylic acid, where the acid moieties are separated by 34 carbons;
   a light amine; and
   a nitro-substituted aromatic compound as a degassing agent.

2. An electrolyte according to claim 1, wherein said aliphatic dicarboxylic acid is suberic acid.

3. An electrolyte according to claim 1, wherein said aliphatic dicarboxylic acid is azelaic acid.

4. An electrolyte according to claim 1, wherein said aliphatic dicarboxylic acid is sebacic acid.

5. An electrolyte according to claim 1, wherein said aliphatic dicarboxylic acid is undecanedioic acid.

6. An electrolyte according to claim 1, wherein said aliphatic dicarboxylic acid is dodecanedioic acid.

7. An electrolyte according to claim 1, wherein said aliphatic dicarboxylic acid is brassylic acid.

8. An electrolyte according to claim 1, wherein said very long chain dicarboxylic acid is dimer acid.

9. An electrolyte according to claim 1, wherein said amine is ammonia.

10. An electrolyte according to claim 1, wherein said amine is diethylamine.

11. An electrolyte according to claim 1, wherein said amine is dimethylamine.

12. An electrolyte according to claim 1, wherein said amine is trimethylamine.

13. An electrolyte according to claim 1, wherein said amine is triethylamine.

14. An electrolyte according to claim 1, wherein said nitro-substituted aromatic compound is 3-nitroacetophenone.

15. An electrolyte according to claim 1, wherein said nitro-substituted aromatic compound is 2-nitroanisole.

16. A conductive electrolyte for high voltage electrolytic capacitors, comprising ethylene glycol, di(ethylene glycol), dimer acid, azelaic acid, boric acid, 3-nitroacetophenone and ammonium hydroxide.

17. An electrolyte according to claim 16, comprising 60–70% by weight ethylene glycol, 10–35% by weight di(ethylene glycol), 0.5–3.0% by weight dimer acid, 2.0–5.0% by weight azelaic acid, no more than 2.0% by weight boric acid, 0.5–1.5% by weight 3-Nitroacetophenone, and 1.0–4.0% by weight ammonium hydroxide (28–30%w/w).

18. An electrolyte according to claim 16, comprising 64.1% by weight ethylene glycol, 27.5% by weight di(ethylene glycol), 1.8% by weight dimer acid, 3.4% by weight azelaic acid, 0.9% by weight boric acid, 0.9% by weight 3-Nitroacetophenone, and 1.4% by weight ammonium hydroxide (28–30%w/w).

19. An electrolytic capacitor impregnated with a conductive electrolyte for high voltage electrolytic capacitors, comprising:

ethylene glycol;

di(ethylene glycol);

boric acid;

an aliphatic dicarboxylic acid of carbon chain length from eight to thirteen;

a very long chain dicarboxylic acid, where the acid moieties are separated by 34 carbons;

a light amine; and a nitro-substituted aromatic compound as a degassing agent.

20. An electrolytic capacitor impregnated with a conductive electrolyte for high voltage electrolytic capacitors, comprising ethylene glycol, di(ethylene glycol), dimer acid, azelaic acid, boric acid, 3-nitroacetophenone and ammonium hydroxide.

21. An implantable cardioverter defibrillator (ICD) comprising an electrolytic capacitor impregnated with a conductive electrolyte for high voltage electrolytic capacitors, comprising:

ethylene glycol;

di(ethylene glycol);

boric acid;

an aliphatic dicarboxylic acid of carbon chain length from eight to thirteen;

a very long chain dicarboxylic acid, where the acid moieties are separated by 34 carbons;

a light amine; and a nitro-substituted aromatic compound as a degassing agent.

22. An implantable cardioverter defibrillator (ICD) comprising an electrolytic capacitor impregnated with a conductive electrolyte for high voltage electrolytic capacitors, comprising ethylene glycol, di(ethylene glycol), dimer acid, azelaic acid, boric acid, 3-nitroacetophenone and ammonium hydroxide.

* * * * *